United States Patent
Asai

(10) Patent No.: US 8,765,821 B2
(45) Date of Patent: Jul. 1, 2014

(54) OIL-IN-WATER TYPE COSMETIC EMULSION

(75) Inventor: Ayumi Asai, Kanagawa (JP)

(73) Assignee: Shiseido Company, Ltd., Tokyo (JP)

( * ) Notice: Subject to any disclaimer, the term of this patent is extended or adjusted under 35 U.S.C. 154(b) by 491 days.

(21) Appl. No.: 12/920,576

(22) PCT Filed: Mar. 11, 2009

(86) PCT No.: PCT/JP2009/001085
§ 371 (c)(1),
(2), (4) Date: Nov. 15, 2010

(87) PCT Pub. No.: WO2009/113302
PCT Pub. Date: Sep. 17, 2009

(65) Prior Publication Data
US 2011/0054041 A1    Mar. 3, 2011

(30) Foreign Application Priority Data
Mar. 11, 2008  (JP) .................... 2008-060824

(51) Int. Cl.
*A61K 8/72* (2006.01)
*A61Q 1/00* (2006.01)
*A61Q 5/06* (2006.01)
*A61Q 5/00* (2006.01)
*A61Q 19/00* (2006.01)

(52) U.S. Cl.
USPC ....................................... 514/772

(58) Field of Classification Search
CPC ......... A61K 8/72; A61K 8/345; A61Q 19/00; A61Q 5/00; A61Q 5/06; A61Q 1/00
USPC ....................................... 514/772
See application file for complete search history.

(56) References Cited

U.S. PATENT DOCUMENTS

| 6,210,693 | B1 | 4/2001 | Inoue et al. | |
| 2004/0077735 | A1* | 4/2004 | Okamoto et al. | ............... 516/53 |

FOREIGN PATENT DOCUMENTS

| JP | 05000933 | | 1/1993 |
| JP | 08059449 | | 3/1996 |
| JP | 08245366 | | 9/1996 |
| JP | 09169618 | * | 6/1997 |
| JP | 09315936 | | 12/1997 |
| JP | 2003081790 | | 3/2003 |
| JP | 2004256515 | | 9/2004 |
| JP | 3634139 | | 3/2005 |
| JP | 2007063140 | | 3/2007 |
| JP | 2007269723 | | 10/2007 |

OTHER PUBLICATIONS

International Preliminary Report on Patentability and Written Opinion of International Application No. PCT/JP2009/001085, dated Nov. 2, 2010.

* cited by examiner

*Primary Examiner* — Kendra D Carter
*Assistant Examiner* — Jason A Deck
(74) *Attorney, Agent, or Firm* — Carol L. Francis; Rudy J. Ng; Bozicevic, Field & Francis LLP

(57) ABSTRACT

The invention provides an oil-in-water type cosmetic emulsion which can be applied to the skin without stickiness, and impart resilient and supple feel to the skin, while having good stability without causing viscosity decrease or separation even during a long-term storage. The oil-in-water type cosmetic emulsion comprises (a) a higher alcohol having 14 to 22 carbon atoms, (b) a hydrophilic polyoxyethylene alkyl ether, and (c) a glycerin monoalkyl ether, wherein alkyl moieties in (b) and (c) are linear saturated alkyl chains, and molar concentrations of (a) to (c) satisfy a relation $[(b)+(c)]/(a)=0.1$ to 1.0, and preferably satisfy a relation $[(a)+(c)]/(b)=3$ to 20.

5 Claims, No Drawings

OIL-IN-WATER TYPE COSMETIC EMULSION

TECHNICAL FIELD

The present invention relates to an oil-in-water type cosmetic emulsion, and more particularly to an oil-in-water type cosmetic emulsion which can achieve resilient and supple feel to a site to which the emulsion is applied without addition of an agent, a powder or a film forming agent thereto.

BACKGROUND ART

A major purpose of cosmetics is retardation, prevention, concealment, or the like of decline in supple, resilience, the appearance of wrinkles or the like associated with aging or the like.

As effective agents therefor, active ingredients derived from crude drugs as well as vitamin A and derivatives thereof are known. Patent Document 1 describes improvement in the skin permeation of a vitamin A ester by addition of casein. However it is difficult to add such ingredients to cosmetics and maintain them stably in a condition effective for the skin.

Although, for example, Patent Document 2 describes a technology by which hydrolysis of a vitamin A ester is prevented and stabilized by adding an antioxidant and a certain amount of a nonionic surfactant, addition of an emulsifier indispensable for a cosmetic emulsion is restricted, and therefore cosmetics that are desirable in terms of viscosity, feel, and the like cannot always be obtained. Furthermore, in order to have the agents clearly exhibit their effects, continuous application is necessary, and even from the viewpoint of encouraging continuous use thereof, it is an important factor for cosmetics that a user can perceive recovery of supple feel or resilience in a relatively short time after the application.

As ingredients which can impart a supple or resilient feel in a shorter time, for example, a film forming ingredient, such as polyvinyl alcohol, sodium alginate, mucopolysaccharides or collagen, an eggshell protein, and degradation products thereof, and an acrylic resin, a spherical or other-shaped powder (Patent Document 3), and cross-linked type methylpolysiloxane (Patent Document 4) have been used so far.

Further, a cosmetic composition prepared by combining an oily base containing an ester of dimer acid and/or dimer diol superior in a water-holding property (Patent Document 5), with a film forming ingredient as described above and a moisturizing ingredient is known to be able to impart a good luster feel or supple feel to the skin (Patent Document 6).

However, when these conventional ingredients are added in amounts that realize a sufficient supple or resilient feel, there have been such problems as streaking or stickiness at application, poor stability during a long-term storage, and an influence on the stability of other ingredients to be added.

Patent Document 1: JP-A-Hei 8-245366
Patent Document 2: JP-B-3634139
Patent Document 3: JP-A-Hei 5-933
Patent Document 4: JP-A-Hei 9-315936
Patent Document 5: JP-A-2004-256515
Patent Document 6: JP-A-2007-269723

DISCLOSURE OF THE INVENTION

Problems to be Solved by the Invention

The present invention has been made to solve conventional problems as described above, and an object thereof is to provide an oil-in-water type cosmetic emulsion which can impart resilience and a supple feel to the skin and exhibit good stability without relying on the presence or absence of agents such as vitamin A, or on a film forming ingredient or a powder.

Means for Solving the Problems

The present inventors have intensively studied to solve the problems and found that a composition prepared with a higher alcohol, a polyoxyethylene alkyl ether, and a glycerin monoalkyl ether has the effect of imparting resilience and a supple feel to the skin, and further that long-term stability is maintained by selecting a specific ratio among the same.

More specifically, the present invention is an oil-in-water type cosmetic emulsion comprising:
(a) one or more of higher alcohols having 14 to 22 carbon atoms,
(b) one or more of hydrophilic polyoxyethylene alkyl ethers, and
(c) one or more of glycerin monoalkyl ethers,
wherein alkyl moieties in (b) and (c) are linear saturated alkyl groups, and the molar concentrations of (a) to (c) satisfy the relation $[(b)+(c)]/(a)=0.1$ to $1.0$.

Further, in the cosmetic emulsion according to the present invention, the molar concentrations of (a) to (c) preferably also satisfy the relation $[(a)+(c)]/(b)=3$ to $9$.

Effects of the Invention

The present invention can provide an oil-in-water type cosmetic emulsion that can impart resilient and supple feel to the skin without relying on the presence or absence of agents such as vitamin A, a film forming ingredient, or the like which have been contained in conventional cosmetics having wrinkles-improving effects, and exhibit non-stickiness and good stability even during a long-term storage without causing viscosity decrease or separation.

BEST MODE FOR CARRYING OUT THE INVENTION

The present invention will now be described in more detail.

The cosmetic emulsion according to the present invention contains (a) one or more of higher alcohols having 14 to 22 carbon atoms (hereinafter referred to as a "higher alcohol"). The higher alcohol (a) preferably contains an alkyl moiety consisting of a linear saturated (single-bonded) alkyl chain. Examples thereof include myristyl alcohol, cetyl alcohol, stearyl alcohol, behenyl alcohol, and oleyl alcohol. Among these, one or more of cetyl alcohol, stearyl alcohol, and behenyl alcohol are preferably included.

According to the present invention, the content of the higher alcohol (a) is preferably 0.1 to 7.0% by mass, and more preferably 0.2 to 6.0% by mass.

The cosmetic emulsion of the present invention contains (b) one or more of hydrophilic polyoxyethylene alkyl ethers (hereinafter referred to as a "polyoxyethylene alkyl ether"). The polyoxyethylene alkyl ether (b) to be used in the present invention is hydrophilic ones constructed with a linear saturated (single-bonded) alkyl chain and a polyoxyethylene chain bonded together by an ether bond. The term "hydrophilic" as used in the present invention means that the HLB value determined by a relative strength of a hydrophilic group and a hydrophobic group is larger than 10.

Examples of the polyoxyethylene alkyl ether (b) include polyoxyethylene(10) stearyl ether, polyoxyethylene(11) stearyl ether, polyoxyethylene(20) stearyl ether, polyoxyethylene(30) stearyl ether, polyoxyethylene(20) behenyl ether, and polyoxyethylene(30) behenyl ether.

Further, as the polyoxyethylene alkyl ether (b) in the present invention, ones having an average number of moles of a polyoxyethylene chain added of 10 to 30 are preferable, and polyoxyethylene(20) stearyl ether and polyoxyethylene(20) behenyl ether are especially preferable.

In the present invention, the content of the polyoxyethylene alkyl ether (b) is preferably 0.01 to 3% by mass, and more preferably 0.05 to 2% by mass.

The cosmetic emulsion of the present invention contains (c) one or more of glycerin monoalkyl ethers (hereinafter referred to as "glycerin monoalkyl ether"). The glycerin monoalkyl ether (c) to be used in the present invention is constructed with a linear saturated (single-bonded) alkyl chain and glycerin bonded together by an ether bond. Examples thereof include glycerin monocetyl ether (chimyl alcohol) and glycerin monostearyl ether (batyl alcohol). Among these, glycerin monostearyl ether is preferable.

In the present invention, the content of the glycerin monoalkyl ether (c) is preferably 0.01 to 5% by mass, and more preferably 0.02 to 3% by mass.

The molar concentrations of (a) to (c) in the cosmetic emulsion of the present invention satisfy the relation [(b)+(c)]/(a)=0.1 to 1.0, more preferably [(b)+(c)]/(a)=0.1 to 0.9, and most preferably 0.2 to 0.8. If the value of [(b)+(c)]/(a) is less than 0.1, a higher alcohol tends to precipitate during a long-term storage, and if the value exceeds 1.0, deterioration in conditions such as separation or viscosity change at a high temperature may take place; both cases provide poor stability.

Further, the molar concentrations of (a) to (c) in the cosmetic emulsion of the present invention also satisfy preferably the relation [(a)+(c)]/(b)=3 to 20, and more preferably [(a)+(c)]/(b)=5 to 19. If the value of [(a)+(c)]/(b) is less than 3, a stable emulsion may not be obtained, and a supple feel and stickiness may also become unsatisfactory. If the value of [(a)+(c)]/(b) exceeds 20, a stable emulsion may not be obtained, and a toned feel may become inferior.

There is no particular restriction on embodiments of an oil-in-water type cosmetic emulsion of the present invention, and it can be used in a form suitable for an intended embodiment, such as a milky lotion, a cream, a serum, a foundation, a makeup base, a lipstick, a hair styling agent, and a hair care agent. Among others, as application to the skin, the use for a milky lotion, a cream, a serum, a foundation, a makeup base, and a lipstick is preferable.

The cosmetic emulsion of the present invention may contain, in addition to the above essential ingredients, a powder, an oil, an active agent, a moisturizing agent, an agent, a film forming agent, a sequestering agent, a lower alcohol, a higher alcohol having a branched chain or a multiple bond, a polyhydric alcohol, an antioxidant, a preservative, a fragrance, or the like according to need, as long as not interfering with the effects of the cosmetic emulsion.

EXAMPLES

The present invention will now be described in more detail by way of Examples thereof, but the present invention is not limited by the examples in any way. The content of an ingredient is expressed in % by mass unless otherwise specified.

Further, in the following tables,
*1 means: having an alkyl moiety consisting of a linear saturated alkyl chain;
*2 means: having an alkyl moiety consisting of a branched alkyl chain; and
*3 means: having an alkyl moiety consisting of an unsaturated alkyl chain.

Examples 1 to 4, Comparative Examples 1 to 8

Oil-in-water type cosmetic emulsions were prepared according to the formulas shown in the following Tables 1 to 3 and according to the method described later.

Then the properties of these oil-in-water type cosmetic emulsions were evaluated. The results are also shown in Tables 1 to 3. The evaluation items were: condition immediately after the preparation, supple feel, absence of stickiness, absence of streaking, and stability over time of emulsion condition, and evaluation methods for these items will be described below.

(Condition Immediately after the Preparation)

After the preparation of a test sample, by microscopic and macroscopic observations, the presence or absence of abnormality in appearance, such as coagulation or flocculation of emulsion particles, crystal precipitation, and separation was evaluated.

A (Good): No abnormality.

B (Slightly poor): Minor abnormality is found in emulsion particles or appearance.

C (Poor): Obvious abnormality is found in emulsion particles or/and appearance.

(Supple Feel)

Supple feel after application to the skin was evaluated by a 20-membered expert panel.

A (Good): 15 or more members felt supple.

B (Slightly poor): 8 to 14 (both inclusive) members felt supple.

C (Poor): 7 or fewer members felt supple.

(Absence of Stickiness)

Absence of stickiness after application to the skin was evaluated by a 20-membered expert panel.

A (Good): 15 or more members did not feel sticky.

B (Slightly poor): 8 to 14 (both inclusive) members did not feel sticky.

C (Poor): 7 or fewer members did not feel sticky.

(Absence of Streaking)

Absence of streaking after application to the skin was evaluated by a 20-membered expert panel.

A (Good): 15 or more members did not feel streaking.

B (Slightly poor): 8 to 14 (both inclusive) members did not feel streaking.

C (Poor): 7 or fewer members did not feel streaking.

(Stability Over Time of Condition)

A sample was stored at 50° C. for 3 months and the stability thereof was evaluated.

A (Good): There is no change in appearance, and the increase or decrease in viscosity from baseline is less than 25%.

B (Slightly poor): Slight oil floating is found at the gas-liquid interface, or/and the increase or decrease in viscosity is 25% or more and less than 50%.

C (Poor): Separation is found or the increase or decrease in viscosity is 50% or more.

(Production Method)

The ingredients 13 to 21 were dissolved uniformly and heated to 70° C., to which the ingredients 1 to 12 mixed at 75° C. were then added under stirring and dispersed uniformly. The mixture was cooled to 40° C. to yield an oil-in-water type cosmetic emulsion.

TABLE 1

| | | Example | | | |
|---|---|---|---|---|---|
| | | 1 | 2 | 3 | 4 |
| 1 | Behenyl alcohol | 0.5 | — | 1 | 4 |
| 2 | Stearyl alcohol | 0.5 | 0.1 | 0.5 | — |
| 3 | Cetyl alcohol | — | 0.5 | — | — |
| 4 | Polyoxyethylene(20) stearyl ether*1 | 0.6 | 0.4 | — | — |
| 5 | Polyoxyethylene(20) behenyl ether*1 | — | — | 1.2 | 0.9 |
| 6 | Polyoxyethylene(5) stearyl ether*1 | — | — | — | — |
| 7 | Polyoxyethylene(20) stearate*1 | — | — | — | — |
| 8 | Polyoxyethylene(20) isostearyl ether*2 | — | — | — | — |
| 9 | Glycerin monostearyl ether*1 | 0.4 | 0.5 | 0.5 | 0.6 |
| 10 | Glycerin monooleyl ether*3 | — | — | — | — |
| 11 | Squalane | 3 | 3 | 6 | 5 |
| 12 | Pentaerythrityl tetraoctanoate | 5 | — | 2 | 20 |
| 13 | Decamethylcyclopentasiloxane | — | 3 | 2 | 5 |
| 14 | Dimer dilinoleate (phytosteryl/isostearyl/cetyl/stearyl/behenyl) | — | — | — | — |
| 15 | Polyvinyl alcohol | — | — | — | — |
| 16 | Glycerin | — | 3 | 5 | 10 |
| 17 | Butylene glycol | — | 15 | 5 | 10 |
| 18 | Ethanol | 5 | 3 | — | — |
| 19 | Xanthan gum | 0.05 | 0.1 | 0.02 | — |
| 20 | Buffer agent | qs | qs | qs | qs |
| 21 | Preservative | qs | qs | qs | qs |
| 22 | Chelating agent | qs | qs | qs | qs |
| 23 | Water | Balance | Balance | Balance | Balance |
| | [(b) + (c)]/(a) (Molar concentration) | 0.5 | 0.74 | 0.5 | 0.2 |
| | [(a) + (c)]/(b) (Molar concentration) | 8.72 | 11.18 | 6.4 | 18.78 |
| | Condition immediately after the preparation | A | A | A | A |
| | Toned feel | A | A | A | A |
| | Absence of stickiness | A | A | A | A |
| | Absence of streaking | A | A | A | A |
| | Stability over time of condition | A | A | A | A |

TABLE 2

| | | Comparative Example | | | |
|---|---|---|---|---|---|
| | | 1 | 2 | 3 | 4 |
| 1 | Behenyl alcohol | 0.5 | 4 | 1 | 0.5 |
| 2 | Stearyl alcohol | 0.5 | — | 0.5 | 0.5 |
| 3 | Cetyl alcohol | — | — | — | — |
| 4 | Polyoxyethylene(20) stearyl ether*1 | 0.6 | — | — | — |
| 5 | Polyoxyethylene(20) behenyl ether*1 | — | 1 | — | — |
| 6 | Polyoxyethylene(5) stearyl ether*1 | — | — | 0.5 | — |
| 7 | Polyoxyethylene(20) stearate*1 | — | — | — | 0.6 |
| 8 | Polyoxyethylene(20) isostearyl ether*2 | — | — | — | — |
| 9 | Glycerin monostearyl ether*1 | 1.1 | 0.1 | 0.5 | 0.4 |
| 10 | Glycerin monooleyl ether*3 | — | — | — | — |
| 11 | Squalane | 3 | 5 | 6 | 3 |
| 12 | Pentaerythrityl tetraoctanoate | 5 | 20 | 2 | 5 |
| 13 | Decamethylcyclopentasiloxane | — | 5 | 2 | — |
| 14 | Dimer dilinoleate (phytosteryl/isostearyl/cetyl/stearyl/behenyl) | — | — | — | — |
| 15 | Polyvinyl alcohol | — | — | — | — |
| 16 | Glycerin | — | 10 | 5 | — |
| 17 | Butylene glycol | — | 10 | 5 | — |
| 18 | Ethanol | 5 | — | — | 5 |
| 19 | Xanthan gum | 0.05 | — | 0.02 | 0.05 |
| 20 | Buffer agent | qs | qs | qs | qs |
| 21 | Preservative | qs | qs | qs | qs |
| 22 | Chelating agent | qs | qs | qs | qs |
| 23 | Water | Balance | Balance | Balance | Balance |
| | [(b) + (c)]/(a) (Molar concentration) | 1.1 | 0.09 | 0.3 | 0.34 |
| | [(a) + (c)]/(b) (Molar concentration) | 12.62 | 15.15 | — | — |
| | Condition immediately after the preparation | B | A | C | A |
| | Toned feel | A | A | B | C |
| | Absence of stickiness | A | A | B | A |
| | Absence of streaking | A | A | A | A |
| | Stability over time of condition | C | C | C | A |

TABLE 3

| | | Comparative Example | | | |
|---|---|---|---|---|---|
| | | 5 | 6 | 7 | 8 |
| 1 | Behenyl alcohol | 0.5 | 0.5 | 0.5 | 0.5 |
| 2 | Stearyl alcohol | 0.5 | 0.5 | 0.5 | 0.5 |
| 3 | Cetyl alcohol | — | — | — | — |
| 4 | Polyoxyethylene(20) stearyl ether*1 | — | — | — | 0.6 |
| 5 | Polyoxyethylene(20) behenyl ether*1 | — | — | — | — |
| 6 | Polyoxyethylene(5) stearyl ether*1 | — | — | — | — |
| 7 | Polyoxyethylene(20) stearate*1 | 0.6 | 0.6 | — | — |
| 8 | Polyoxyethylene(20) isostearyl ether*2 | — | — | 0.6 | — |
| 9 | Glycerin monostearyl ether*1 | 0.4 | 0.4 | 0.4 | — |
| 10 | Glycerin monooleyl ether*3 | — | — | — | 0.4 |
| 11 | Squalane | 3 | 3 | 3 | 3 |
| 12 | Pentaerythrityl tetraoctanoate | 5 | 5 | 5 | 5 |
| 13 | Decamethylcyclopentasiloxane | — | — | — | — |
| 14 | Dimer dilinoleate (phytosteryl/isostearyl/cetyl/stearyl/behenyl) | — | 3 | — | — |
| 15 | Polyvinyl alcohol | 0.5 | — | — | — |
| 16 | Glycerin | — | — | — | — |
| 17 | Butylene glycol | — | — | — | — |
| 18 | Ethanol | 5 | 5 | 5 | 5 |
| 19 | Xanthan gum | 0.05 | 0.05 | 0.05 | 0.05 |
| 20 | Buffer agent | qs | qs | qs | qs |
| 21 | Preservative | qs | qs | qs | qs |
| 22 | Chelating agent | qs | qs | qs | qs |
| 23 | Water | Balance | Balance | Balance | Balance |
| | [(b) + (c)]/(a) (Molar concentration) | 0.34 | 0.34 | 0.34 | 0.15 |
| | [(a) + (c)]/(b) (Molar concentration) | — | — | — | 6.49 |
| | Condition immediately after the preparation | A | A | C | B |
| | Toned feel | A | A | B | A |
| | Absence of stickiness | B | C | B | A |
| | Absence of streaking | C | A | B | A |
| | Stability over time of condition | A | A | C | C |

From the results obtained above, if a cosmetic emulsion contains all of the ingredients (a) to (c) of the present invention, and the molar concentrations thereof satisfy a defined relation (Examples 1 to 4), the condition immediately after the preparation, the supple feel, the absence of stickiness, the absence of streaking, and the stability over time of condition were superior, while the stability over time was maintained.

In contrast, in Comparative Examples 1 and 2, the ratio of the total molar concentration of the ingredient (b) and the ingredient (c) to the molar concentration of the ingredient (a) ([(b)+(c)]/(a)) was outside the range defined according to the present application, and consequently both the emulsions were inferior in stability over time. In Comparative Example 3, the added polyoxyethylene alkyl ether was not hydrophilic (HLB=7), and consequently a good emulsified state could not be established. Further, in Comparative Example 4, where a polyoxyethylene alkyl ester was used instead of the polyoxyethylene alkyl ether (b), a supple feel could not be obtained. In Comparative Examples 5 and 6, where polyvinyl alcohol or a water-holding oil, which has conventionally been known to impart a supple feel, was added to Comparative Example 4, a supple feel was imparted indeed, but stickiness and streaking were also imparted, and suitable cosmetics could not be obtained.

Further, in Comparative Example 7, where polyoxyethylene isostearyl ether having a branched alkyl chain was used instead of the polyoxyethylene alkyl ether (b), a homogeneous emulsified condition could not be obtained, and an emulsion in a stable condition was not obtained. Meanwhile, in Comparative Example 8, where glycerin monooleyl ether having an alkyl chain having a double bond was used instead of the glycerin monoalkyl ether (c), an emulsion having superior stability over time of the condition could not be obtained.

Further, in Comparative Examples 9 and 10, where the ratio of the total molar concentration of the ingredient (a) and the ingredient (c) to the molar concentration of the ingredient (b), ([(a)+(c)]/(b)), was outside the preferred range, a homogeneous emulsified condition could not be obtained, and although the emulsion was applied to the skin, it was far from a satisfactory cosmetic in terms of a supple feel and absence of stickiness.

Some formula examples of the present invention will now be described below as Examples. Cosmetics in the Examples were prepared by a conventional method, and were good in the condition immediately after the preparation, a supple feel, absence of stickiness, absence of streaking, and stability over time of condition.

Example 5 (Milky Lotion)

| Ingredients | Content (% by mass) |
| --- | --- |
| 1 Dimethylpolysiloxane | 2 |
| 2 Hardened oil | 3 |
| 3 Squalane | 6 |
| 4 Pentaerythritol tetra(2-ethylhexanoate) | 2 |
| 5 Behenyl alcohol | 1 |
| 6 Batyl alcohol*1 | 0.4 |
| 7 Polyoxyethylene(30) behenyl ether*1 | 0.7 |
| 8 Glycerin | 5 |
| 9 1,3-Butylene glycol | 7 |
| 10 Erythritol | 2 |
| 11 Sarcosine | 1 |
| 12 Sodium carboxyvinyl polymer | 0.1 |
| 13 Sodium metaphosphate | 0.05 |
| 14 Phenoxy ethanol | 0.5 |
| 15 Purified water | Balance |

Example 6 (Cream)

| Ingredients | Content (% by mass) |
| --- | --- |
| 1 Squalane | 2 |
| 2 Pentaerythrityl tetraoctanoate | 15 |
| 3 Methylpolysiloxane | 4 |
| 4 Decamethylcyclopentasiloxane | 3 |
| 5 Methyl phenyl polysiloxane | 1 |
| 6 Behenyl alcohol | 3 |
| 7 Stearyl alcohol | 0.5 |
| 8 Batyl alcohol*1 | 1.7 |
| 9 Polyoxyethylene(20) behenyl ether*1 | 1 |
| 10 Glycerin | 10 |
| 11 Butylene glycol | 5 |
| 12 Tranexamic acid | 2 |
| 13 Carnosine | 1.5 |
| 14 Dipotassium glycyrrhizinate | 0.1 |
| 15 Sodium pyrrolidone carboxylate | 0.1 |
| 16 Potassium carboxyvinyl polymer | 0.1 |
| 17 Paraben | 0.2 |
| 18 Sodium metaphosphate | 0.05 |
| 19 Purified water | Balance |

Example 7 (Sunscreen Cosmetic)

| Ingredients | Content (% by mass) |
| --- | --- |
| 1 Octyl methoxycinnamate | 5 |
| 2 Octocrylene | 5 |
| 3 t-Butyl methoxybenzoyl methane | 2 |
| 4 Phenylbenzimidazole sulfonic acid | 2 |
| 5 Diisopropyl sebacate | 2 |
| 6 Decamethylcyclopentasiloxane | 5 |
| 7 Glyceryl diisostearate | 1 |
| 8 Jojoba oil | 2 |
| 9 Cetostearyl alcohol | 2 |
| 10 Polyoxyethylene(20) stearyl ether*1 | 1.5 |
| 11 Polyoxyethylene(20) sorbitan monostearate | 0.2 |
| 12 Batyl alcohol*1 | 0.5 |
| 13 Glyceryl monostearate | 0.3 |
| 14 Triethanolamine | 1.5 |
| 15 Butylene glycol | 10 |
| 16 Silicic anhydride | 2 |
| 17 Winged bean extract | 0.5 |
| 18 Ethanol | 5 |
| 19 Tocopherol acetate | 0.1 |
| 20 Sodium pyrosulfite | 0.01 |
| 21 Phenoxyethanol | 0.3 |
| 22 Sodium edetate | 0.05 |
| 23 Buffer agent | qs |
| 24 Purified water | Balance |

Example 8 (Makeup Base)

| Ingredients | Content (% by mass) |
| --- | --- |
| 1 Decamethylcyclopentasiloxane | 10 |
| 2 Trimethylsiloxysilicate | 0.5 |
| 3 Methylpolysiloxane | 2 |
| 4 Cross-linked methylpolysiloxane | 3 |
| 5 Diisostearyl malate | 2 |
| 6 Cetanol | 1 |
| 7 Stearyl alcohol | 1 |
| 8 Batyl alcohol*1 | 1 |
| 9 Self-emulsification type glycerin monostearate | 1 |
| 10 Batyl alcohol*1 | 0.7 |
| 11 Stearic acid | 0.5 |
| 12 Behenic acid | 0.5 |
| 13 Polyoxyethylene(15) stearyl ether | 0.5 |
| 14 Glycerin | 1 |
| 15 Propylene glycol | 5 |
| 16 Bentonite | 1 |
| 17 Nicotinamide | 1 |
| 18 Xanthan gum | 0.1 |
| 19 Silicic anhydride | 5 |
| 20 Talc | 1 |
| 21 Titanium oxide | 1 |
| 22 Yellow iron oxide-coated titanated mica | 0.5 |
| 23 Ethanol | 5 |
| 24 Phenoxyethanol | 0.5 |

-continued

| Ingredients | Content (% by mass) |
|---|---|
| 25 Sodium edetate | 0.1 |
| 26 Purified water | Balance |

The invention claimed is:

1. An oil-in-water type cosmetic emulsion comprising:
   (a) 0.1-7% by mass of one or more of higher alcohols having 14 to 22 carbon atoms,
   (b) 0.05-2% by mass of one or more of hydrophilic polyoxyethylene alkyl ethers, and
   (c) 0.01-5% by mass of one or more of glycerin monoalkyl ethers, wherein alkyl moieties in (b) and (c) are linear saturated alkyl chains, and molar concentrations of (a) to (c) satisfy a relation $[(b)+(c)]/(a)=0.1$ to $1.0$, and
   wherein the molar concentrations of (a) to (c) satisfy a relation $[(a)+(c)]/(b)=5$ to $19$.

2. The oil-in-water type cosmetic emulsion according to claim 1, wherein the alkyl moiety in the (a) is a linear saturated alkyl chain.

3. The oil-in-water type cosmetic emulsion according to claim 1, wherein the molar concentrations of (a) to (c) satisfy a relation $[(b)+(c)]/(a)=0.1$ to $0.9$.

4. The oil-in-water type cosmetic emulsion according to claim 1, wherein (c) is glycerin monostearyl ether.

5. The oil-in-water type cosmetic emulsion according to claim 1, wherein the average number of moles of polyoxyethylenes added in (b) is 10 to 30.

\* \* \* \* \*